United States Patent [19]

Fukui et al.

[11] 4,230,725

[45] Oct. 28, 1980

[54] ANTIVIRAL AGENT

[75] Inventors: Masaru Fukui, Takarazuka; Shigeo Ogino, Nishinomiya; Hisao Yamamoto, Kobe, all of Japan

[73] Assignees: Sumitomo Chemical Company, Limited, Osaka; Kao Soap Company, Limited, Tokyo, both of Japan

[21] Appl. No.: 939,682

[22] Filed: Sep. 5, 1978

Related U.S. Application Data

[63] Continuation-in-part of Ser. No. 883,743, Mar. 6, 1978, abandoned.

[30] Foreign Application Priority Data

Mar. 10, 1977 [JP] Japan .................................. 52/26730

[51] Int. Cl.³ ............................................. A61K 31/13
[52] U.S. Cl. ...................................................... 424/325
[58] Field of Search ......................................... 424/325

[56] References Cited

U.S. PATENT DOCUMENTS

| | | | |
|---|---|---|---|
| 3,397,233 | 8/1968 | Cairns ................................ | 424/325 |
| 3,592,934 | 7/1971 | Prichard ............................ | 424/325 |

FOREIGN PATENT DOCUMENTS 53-50150  5/1978  Japan .

*Primary Examiner*—Jerome D. Goldberg
*Attorney, Agent, or Firm*—Stevens, Davis, Miller & Mosher

[57] ABSTRACT

Antiviral agents containing an effective amount of 1-amino-2,4-ethanobicyclo[3,3,1]nonane or salts thereof which are effective for the treatment or prevention of infectious diseases caused by herpes or influenza virus.

1 Claim, 1 Drawing Figure

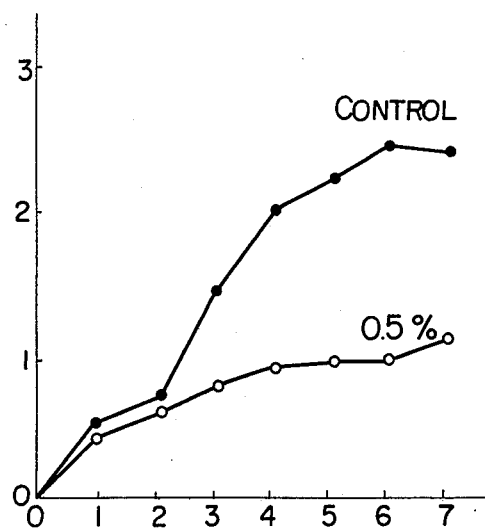

ANTIVIRAL AGENT

CROSS REFERENCE TO RELATED APPLICATION

This is a continuation-in-part of co-pending application Ser. No. 883,743 filed on Mar. 6, 1978, now abandoned.

The present invention relates to an antiviral composition which comprises 1-amino-2,4-ethanobicyclo[3,3,1-]nonane or its salt as an active ingredient and pharmaceutically acceptable carriers.

1-Amino-2,4-ethanobicyclo[3,3,1]nonane hydrochloride (hereinafter referred to as compound A), which is the hydrochloric acid salt of the said 1-amino-2,4-ethanobicyclo[3,3,1]nonane, can be synthesized according to the method described in Japanese Patent Laid-Open (Kokai) No. 50150/1978. As to the antiviral activity of the compound A, the activity against Newcastle disease virus is reported in said Japanese Patent Laid-Open (Kokai) No. 50150/1978, but the activity against other viruses has never been reported.

As the result of an extensive study on the antiviral activity of the compound A, the inventors found a very strong antiviral activity of the compound A against herpes and influenza viruses as well, and attained the present invention.

It is a well-known fact that some of the so-called "caged compounds" such as amantadine have the antiviral activities against RNA viruses, but those having an antiviral activities against DNA virus are not known. The compound A combines an antiviral activity against influenza virus belonging to the RNA virus and a very strong antiviral activity against herpes virus belonging to the DNA virus. Accordingly, the compound A is a very effective antiviral agent.

Next, the antiviral activity, effective dosages and toxicities of the compound A will be described.

EXAMPLE 1

Effects of the compound A on the growth of herpes virus in tissue cultures

The antiviral activity was examined by the tube dilution method. HeLa cells and KB cells for the assay were cultured in YLE medium and Eagle MEM medium in vitro, respectively, containing 10% fetal calf serum. After the cells were grown in a monolayer form, the medium was exchanged to the fresh medium supplemented with 2% fetal calf serum, and then about 1000 $TCD_{50}$ of herpes simplex virus type I (HF strain) and the test compound were added. After 72 hours' incubation at 37° C., the cytotoxicity of the compound and the virus induced cytopathic effect (CPE) were observed microscopically.

The antiviral activity was expressed in minimum virus growth inhibitory concentration (MIC) and minimum cytotoxic concentration (MCC) in Table 1.

TABLE 1

The effect of the compound A on growth of *Herpes simplex* virus

| Compound | Host cells | MIC (μg/ml) | MCC (μg/ml) |
|---|---|---|---|
| Compound A | HeLa | 2.5 | 100 |
|  | KB | 2.5 | 100 |
| Amantadin hydrochlo | HeLa | 50 | >50 |
|  | KB | 50 | >50 |

EXAMPLE 2

Therapeutic effects of the compound A on experimental herpes virus infection

The therapeutic effects were examined with two experimental infections.

(i) Effects on herpes keratitis

After 2% cocaine was applied to the eyes of a rabbit anesthetized with barbital, the corneal epithelium of each eye was scratched and infected with herpes simplex virus type I (HF strain).

One of the infected eyes was used for treatment with the compound A and the other was used for viral control.

The treatment with the compound A was carried out as follows: Twelve hours after virus infection, 0.5% eye lotion of the compound A in 1.4% polyvinyl alcohol was applied every two hours, five times a day during seven days.

For seven days after infection, the lesions on the conjunctiva, cornea and iris were daily observed visually prior to the first treatment and recorded according to the scoring method.

Separately from this, eyes of a rabbit were scratched but not infected with virus, one of the eyes was similarly treated with the compound A and the other eye was treated with 1.4% polyvinyl alcohol as toxicity control.

The single FIGURE shows the therapeutic effect of the compound A on herpes keratitis. The abscissa indicates days elapsed after viral infection and the ordinate indicates the scores [0 (normal)-4 (maximal severity)]. The mark—○—indicates the scroes of the eye treated with an eye lotion containing 0.5% compound A and the mark—●—indicates that of control.

One half percent eye lotion of the compound A did not prolong the cure period as compared with the toxicity control, which means that the compound A has no toxicity.

(ii) Effects on herpes encephalitis

Mice were anesthetized with ether and were infected intracerebrally (i.e.) with about 30 $LD_{50}$ of herpes simplex virus type I (HF strain). The infected mice were administered with the compound A according to various therapeutic schedules. The therapeutic effects of the compound A were examined on the basis of the survival ratios at the 3rd week after virus infection and the mean survival days. The results are shown in Table 2.

TABLE 2

Therapeutic effect of the compound A on *herpes encephalitis*

| | Dose[a] (mg/kg) | Admin-[b] istration route | Means[c] survival term (day) | Survival ratio[d] no. of survivors/ no. of total mice |
|---|---|---|---|---|
| Compound A | 5 | i.c. | 8.3 | 6/10 |
|  | 0 |  | 5.7 | 0/10 |
| Compound A | 100 | p.o. | 7.7 | 4/10 |
|  | 0 |  | 5.5 | 0/10 |
| Compound A | 100 | s.c. | 7.6 | 5/10 |
|  | 0 |  | 5.7 | 0/10 |
| Compound A | 10 | i.v. | 8.1 | 4/10 |

TABLE 2-continued

Therapeutic effect of the compound A on *herpes encephalitis*

| Dose[a] (mg/kg) | Admin-[b] istration route | Means[c] survival term (day) | Survival ratio[d] no. of survivors/ no. of total mice |
|---|---|---|---|
| 0 | | 5.8 | 0/10 |

[a]Dose of administration
[b]Administration schedule of each route was as follows:
i.c. (intracerebrally): Single administration simultaneously with virus infection.
p.o. (per os): Two administrations per day during 8.5 days from 4 hours after virus infection.
s.c. (subcutaneously): Two administrations per day during 8.5 days from 4 hours after virus infection.
i.v. (intravenously): Single administration 3 hours after virus infection.
[c]The animals were examined for 21 days after infection, and mean survival term was determined.
[d]Survival ratio on the 21st day after virus infection.

EXAMPLE 3

Acute toxicity of the compound A in mice

The acute toxicity of the compound A in mice was obtained as usual and shown in Table 3. In this test, Amantadine hydrochloride (Symmetrel ®) belonging to the same class of caged compounds was used as a control.

TABLE 3

Acute toxicity of the compound A in mice

| Drugs | $LD_{50}$ (mg/kg) | |
|---|---|---|
| | p.o. | i.v. |
| Compound A | 320 | 58 |
| Amantadine hydrochloride | 480 | 86 |

EXAMPLE 4

Effects of the compound A on experimental Influenza virus infection

The antiviral activities were determined by the modified Horsfall's method (Tani et al., Fukuoka Igaku Zasshi, 58, 9 (1967)).

Drug preparation

The compound A and amantadine hydrochloride as a control were dissolved in sterile physiological saline for injection.

Animals ddY male mice weighing about 12 g were used in this study. Ten animals were used at each experiment.

Virus

Influenza $A_oPR/8$ was used.

Drug evaluation

Five $LD_{50}$ of influenza $A_oPR/8$ was used for infecting mice by the aerosol. Subcutaneous drug treatment using various dosages started at 3 hours pre, 2, 6, 18, 30, 42, 54, 66, 78, 90, 102, 114, 126, 138 and 150 hours post infection in order to determine the efficacy of the compound A and amantadine hydrochloride.

Lung lesion score (LLS) was determined 7 days after infection by sacrificing the animals. When the mice were died within 7 days after infection, LLS determination was also carried out.

Results were as follows:

| Exp. No. | Drug dose (mg/kg) | Lung Lesion Score |
|---|---|---|
| 1 | 0 | 4.8 |
| 2 | amantadine HCl (10 mg/kg) | 4.3* |
| 3 | amantadine HCl (25 mg/kg) | 4.1* |
| 4 | amantadine HCl (50 mg/kg) | 4.0* |
| 5 | compd. A (7.5 mg/kg) | 4.4 |
| 6 | compd. A (15 mg/kg) | 4.2* |
| 7 | compd. A (30 mg/kg) | 4.0* |

*$P < 0.05$ (Probability value, Student's t test)

As is apparent from the experimental results, the compound A shows a very strong antiviral activity in vivo as well as in vitro, and can be used for the therapy of human herpes viral diseases, for example herpes keratitis, herpes encephalitis, herpes labialis, and human influenza infections in the pharmaceutical forms such as ointments, eye lotions, injections, orally administrable agents and so on.

The dose of the compound A used in the treatment for adults is varied with administration routes. In the use as eye lotions or ointments, several administrations per day of the dosage level of 0.1–1%, preferably 0.2%, are desirable. When administered orally or subcutaneously, 50–1000 mg, preferably 200 mg per day as total dose is desirable. In the intraveneous administration, 10–50 mg, preferably 10 mg per day is desirable.

The compound A can be formulated into eye lotions, ointments, injections, orally administrable agents and so on in the well-known methods on the analogy of the formulation of representative antiviral agents.

The present invention will be illustrated with reference to the following formulation examples.

Formulation example 1

Eye lotion

Distilled water (800 ml) was placed in a 1000 ml cylinder with ground stopper, and β-phenylethyl alcohol (5 ml) and the compound A (5 g) were added. After the solution was finally made isotonic with sodium chloride, the solution was made up to 1000 ml with distilled water and filtered through a cotton plug. The materials were dealt with aseptically.

Formulation example 2

Ointment

The compound A was triturated with a small amount of liquid paraffin, and then vaseline was added to prepare a 0.5% agent. The materials were dealt with aseptically.

Formulation example 3

Orally administrable agent

| | | |
|---|---|---|
| 1. | 1-Amino-2,4-ethanobicyclo-[3,3,1]nonane hydrochloride | 100 mg |
| 2. | Sucrose | 88 mg |
| 3. | Kaolin | 150 mg |
| 4. | Potato starch | 20 mg |
| 5. | Magnesium stearate | 5 mg |

To a mixture of 1, 2 and 3, 4 was added in a form of 10% starch paste, followed by granulation. The granules obtained were passed through No. 60-mesh (B.S.) sieve and dried to a constant weight. After drying, the granules were passed through No. 16-mesh (B.S.) sieve and mixed with 5 to prepare free-flowing granules which were then pressed by a 7/16" punch into 100-mg tablets. The tablets may be coated as usual, if necessary, with an easily soluble filmforming coating.

Formulation example 4

Injection

Sterile 1-amino-2,4-ethanobicyclo[3,3,1]nonane hydrochloride (10 mg) was aseptically put into a vial which was then sealed to protect it from humidity and microbial contamination. Before use, it is mixed with 2 ml of a 5% injectable glucose solution.

Formulation example 5

Injection

Sterile 1-amino-2,4-ethanobicyclo[3,3,1]nonane hydrochloride (100 mg) was aseptically put into a vial which was then sealed to protect it from humidity and microbial contamination. Before use, it is mixed with 2 ml of a 0.9% saline solution.

What is claimed is:

1. A method for the treatment of infectious diseases caused by herpes virus which comprises administering an amount pharmaceutically effective for the treatment of said infectious diseases of 1-amino-2,4-ethanobicyclo[3,3,1]nonane or its pharmaceutically acceptable salts to a patient suffering from said infectious diseases.

* * * * *